United States Patent [19]

Shinohara

[11] Patent Number: 5,403,947

[45] Date of Patent: Apr. 4, 1995

[54] METHOD OF PRODUCING DICYCLOPENTYLDICHLOROSILANE

[75] Inventor: Toshio Shinohara, Takasaki, Japan

[73] Assignee: Shin-Etsu Chemical Co., Ltd., Tokyo, Japan

[21] Appl. No.: 265,885

[22] Filed: Jun. 27, 1994

[30] Foreign Application Priority Data

Jun. 28, 1993 [JP] Japan .................................. 5-184360

[51] Int. Cl.$^6$ ................................................ C07F 7/08
[52] U.S. Cl. .................................................. 556/479
[58] Field of Search ......................................... 556/479

[56] References Cited

U.S. PATENT DOCUMENTS

| | | | |
|---|---|---|---|
| 4,785,066 | 11/1988 | Maxson | 556/479 X |
| 4,831,081 | 5/1989 | King et al. | 556/479 X |
| 4,847,228 | 7/1989 | Saruyama | 556/479 X |
| 5,142,037 | 8/1992 | Yamazaki et al. | 556/479 |
| 5,328,974 | 7/1994 | McAfee et al. | 556/479 X |

*Primary Examiner*—Paul F. Shaver
*Attorney, Agent, or Firm*—Millen, White, Zelano & Branigan

[57] ABSTRACT

A method of producing dicyclopentyldichlorosilane which comprises reacting cyclopentene and dichlorosilane with each other by using a platinum catalyst and/or a rhodium catalyst in the presence of 1,3-diethinyl-1,1,3,3-tetramethyldisiloxane.

8 Claims, No Drawings

METHOD OF PRODUCING DICYCLOPENTYLDICHLOROSILANE

FIELD OF THE INVENTION

The present invention relates to a method of producing dicyclopentyldichlorosilane and, more particularly, to a novel method in which cyclopentene and dichlorosilane are used to produce dicyclopentyldichlorosilane.

BACKGROUND OF THE INVENTION

Dicyclopentyldichlorosilane is widely used as a basic starting material having high activity in the production of other organosilicon compounds or compounds containing organosilicon groups.

Therefore, it has so far been attempted to produce the dicyclopentyldichlorosilane by the reaction between easily available starting materials, namely cyclopentene and dichlorosilane, and many studies on catalysts for this reaction have been done. However, all the catalysts which have so far been studied do not sufficiently drive the reaction, and so they cannot serve for the industrial use.

Such being the case, the production of said compound has been carried out by another method which uses trichlorosilane and cyclopentene as starting materials. According to this method, trichlorosilane and cyclopentene undergo addition reaction in the presence of a platinum and/or rhodium catalyst to produce cyclopentyltrichlorosilane as an intermediate, and then the intermediate is made to react with cyclopentylmagnesium chloride to give the intended compound. However, this method has a disadvantage in requiring two different reactors since it comprises two different types of reactions, namely addition reaction and Grignard reaction.

Thus, it is still a problem to be solved to produce useful dicyclopentyldichlorosilane by a one-step addition reaction alone.

SUMMARY OF THE INVENTION

As a result of our intensive studies on simple methods for producing dicyclopentyldichlorosilane, it has been found out that dicyclopentyldichlorosilane of high purity can be produced with ease by a one-step addition reaction when 1,3-diethinyl-1,1,3,3-tetramethyldisiloxane is used in combination with a platinum catalyst and/or a rhodium catalyst in order to cause a reaction between cyclopentene and dichlorosilane, thereby achieving the present invention.

Therefore, a first object of the present invention is to provide a simple method of producing dicyclopentyldichlorosilane.

A second object of the present invention is to provide a method of producing dicyclopentyldichlorosilane using easily available cyclopentene and dichlorosilane as starting materials.

The above-described objects are attained by a method of producing dicyclopentyldichlorosilane wherein cyclopentene and dichlorosilane are reacted with each other using a platinum catalyst and/or a rhodium catalyst in the presence of 1,3-diethinyl-1,1,3,3-tetramethyldisiloxane.

DETAILED DESCRIPTION OF THE INVENTION

The method of the present invention is illustrated by the following reaction scheme:

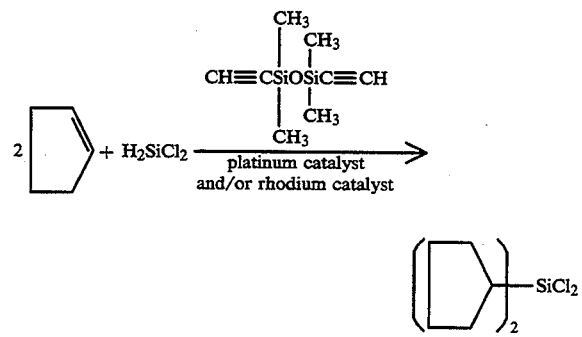

It is effectual to use dichlorosilane in an amount of more than ½ mole per mole of cyclopentene, though the amount is stoichiometrically ½ mole per mole of cyclopentene. More specifically, it is preferable to admit dichlorosilane into a reactor in an amount ranging from more than ½ mole to less than 2 moles, particularly more than ½ to 1 mole, per mole of cyclopentene.

Specific examples of a platinum catalyst which can be used herein include $H_2PtCl_2.6\ H_2O$, Pt-C and $[Pt(CH_2H_4)Cl_2]_2$, and those of a rhodium catalyst which can be used herein include $RhCl(PPh_3)_3$, Rh-C and Rh-alumina. These catalysts may be used alone or as a mixture of two or more thereof.

The proportion of a platinum and/or rhodium catalyst used in the present invention is in the range of $1 \times 10^{-4}$ to 10% by weight, preferably $1 \times 10^{-2}$ to 1% by weight, to the cyclopentene as a starting material. When the catalyst is used in a proportion less than $1 \times 10^{-4}$ % by weight, the reaction speed is extremely slow, so that it becomes difficult to efficiently synthesize the present compound; while proportions of the catalyst increased beyond 10% by weight have disadvantage in economy.

As for the 1,3-diethinyl-1,1,3,3-tetramethyldisiloxane used as catalyst in the present invention, its proportion to cyclopentene as a starting material is also limited for the same reasons as advanced with regard to the platinum and/or rhodium catalyst. Specifically, the proportion of 1,3-diethinyl-1,1,3,3-tetramethyldisiloxane to the cyclopentene is in the range of $1 \times 10^{-4}$ to 50% by weight, preferably $1 \times 10^{-2}$ to 10% by weight.

In case of using a solvent, although any solvent may not be used in the present method, it is desirable to choose the solvent from hydrocarbon solvents such as benzene, toluene, xylene, n-hexane, etc., or from chlorinated solvents such as $CCl_4$, $CHCl_3$, $CH_2Cl_2$, etc. The amount of the solvent used is 0.1 to 100 times, preferably 0.5 to 10 times, by weight as much as that of dichlorosilane as a starting material.

It is desirable that the reaction temperature be in the range of 20° C. to 200° C., preferably −10° C. to 100° C., and particularly preferably 5° to 50° C., and the reaction time be in the range of 10 minutes to 30 hours, preferably 30 minutes to 10 hours, and particularly preferably 30 minutes to 5 hours.

As for the reaction temperature, it should be properly chosen depending on the catalysts used. This is because the reaction does not proceed when the temperature is too low for the reaction system, while too high temperatures cause decomposition of the catalysts used.

In accordance with the present invention, the starting materials used as well as the catalysts used are easily available. Therefore, the present method has considerable significance in the production of dicyclopentyldichlorosilane on an industrial scale.

The present invention will now be illustrated in more detail by reference to the following examples. However, the invention should not be construed as being limited to these examples.

EXAMPLE 1

In a mixture of 136 g (2.00 moles) of cyclopentene, 0.3 g of 1,3-diethinyl-1,1,3,3-tetramethyldisiloxane, 0.1 g of $H_2PtCl_6.6 H_2O$ and 100 g of dichloroethane was blown 101 g (1.00 mole) of dichlorosilane for a period of 2 hours at 40° C. to make the reaction proceed.

At the conclusion of the reaction, the dichloroethane as solvent was distilled away, and the residue was purified in a distilling column. Thus, 50 g of dicyclopentyldichlorosilane having a boiling point of 104° C./5 mmHg was obtained. Yield: 21%.

COMPARATIVE EXAMPLE 1

An experiment was carried out under the same condition as in Example 1, except that 1,3-diethinyl-1,1,3,3-tetramethyldisiloxane was not used. Therein, however, the reaction did not proceed. Thus, the intended dicyclopentyldichlorosilane was not obtained.

COMPARATIVE EXAMPLE 2

Another experiment was carried out under the same condition as in Example 1, except that $H_2PtCl_6.6 H_2O$ was not used. Therein, the reaction did not proceed. Thus, the intended dicyclopentyldichlorosilane was not obtained.

EXAMPLES 2 TO 5 AND COMPARATIVE EXAMPLES 3 TO 6

Cyclopentene in an amount of 136 g (2.00 moles) was made to react with dichlorosilane under various conditions set forth in Table 1, and then the solvent was distilled away. Thus, in analogy with Example 1, dicyclopentyldichlorosilane having a boiling point of 104° C./5 mmHg was obtained in various yields. The yield attained under each reaction condition is shown in Table 1.

trimethylsilyl)acetylene [$(CH_3)_3SiC\equiv CSi(CH_3)_3$; LS-7220, trade name, products of Shin-Etsu Chemical Co., Ltd.], ethinyltrimethylsilane [$(CH_3)_3SiC\equiv CH$; LS-610, trade name, products of Shin-Etsu chemical Co., Ltd.] and 1,3-divinyl-1,1,3,3-tetramethyldisiloxane [$CH_2=CH-Si(CH_3)_2-O-Si(CH_3)_2-CH=CH_2$; LS-7250, trade name, products of Shin-Etsu Chemical Co., Ltd.], respectively. Herein, however, the intended dicyclopentyldichlorosilane was not produced at all, but cyclopentyldichlorosilane was produced in respective yields of 73%, 70% and 69%.

APPLICATION EXAMPLE 1

Into a mixture of 32 g (1.00 mole) of methanol and 60 g (1.00 mole) of urea was dripped 118.7 g (0.50 mole) of dicyclopentyldichlorosilane produced in the same manner as in Example 1 for a period of 1 hour at 40°C.

After the dripping operation, the reaction mixture was ripened by 2 hours heating at 65° C. The salt produced therein was removed, and then the reaction product was purified in a distilling column. Thus, 112 g of dicyclopentyldimethoxysilane having a boiling point of 103° C./5 mmHg was obtained. Yield: 98%.

What is claimed is:

1. A method of producing dicyclopentyldichlorosilane, comprising the step of making a reaction take place between cyclopentene and dichlorosilane using a platinum catalyst, a rhodium catalyst or a mixture thereof in the presence of 1,3-diethinyl-1,1,3,3-tetramethyldisiloxane.

2. The method of claim 1, wherein the platinum catalyst, the rhodium catalyst or the mixture thereof is used in a proportion ranging from $1\times 10^{-4}$ to 10% by weight to the cyclopentene.

3. The method of claim 1, wherein 1,3-diethinyl-1,1,3,3-tetramethyldisiloxane is used in a proportion ranging from $1\times 10^{-4}$ to 50% by weight to the cyclopentene.

4. The method of claim 1, wherein the platinum catalyst is selected from the group consisting of $H_2PtCl_2.6 H_2O$, Pt-C and $[Pt(CH_2H_4)Cl_2]_2$.

5. The method of claim 1, wherein the rhodium catalyst is selected from the group consisting of $RhCl(PPh_3)_3$, Rh-C and Rh-alumina.

6. The method of claim 1, wherein the amount of dichlorosilane for the reaction is more than ½ mole to less than 2 moles per mole of cyclopentene.

7. The method of claim 1, wherein the amount of 1,3-diethinyl-1,1,3,3-tetramethyldisiloxane is $1\times 10^{-2}$ to 10% by weight based on the amount of cyclopentene.

8. The method of claim 1, wherein the reaction temperature is from −20° C. to 200° C. and the reaction time is from 10 minutes to 30 hours.

TABLE 1

| | Amount (g) of 1,3-Diethinyl-1,1,3,3-tetramethyldisiloxane | Platinum or Rhodium Catalyst | | Solvent | | Amount (mole) of Dichlorosilane | Reaction Temp. (°C.) | Reaction Time (hr) | Yield (%) |
|---|---|---|---|---|---|---|---|---|---|
| | | Species | Amount (g) | Species | Amount (g) | | | | |
| Example 2 | 0.3 | $H_2PtCl_6.6H_2O$ | 0.5 | not used | | 1.05 | 20 | 2.0 | 20 |
| Example 3 | 0.5 | $RhCl(PPh_3)_3$ | 0.3 | $CCl_4$ | 200 | 1.00 | 45 | 2.0 | 16 |
| Example 4 | 1.0 | $RhCl(PPh_3)_3$ | 0.3 | not used | | 1.05 | 10 | 2.0 | 18 |
| Example 5 | 0.7 | 5% Rh-C | 1.0 | $n-C_6H_{14}$ | 150 | 1.05 | 20 | 2.0 | 13 |
| Comparative Example 3 | not used | $H_2PtCl_6.6H_2O$ | 0.5 | not used | | 1.00 | 20 | 3.0 | 0 |
| Comparative Example 4 | not used | $RhCl(PPh_3)_3$ | 0.3 | $CCl_4$ | 200 | 1.10 | 45 | 2.0 | 0 |
| Comparative Example 5 | not used | 5% Rh-C | 1.0 | $n-C_6H_{14}$ | 150 | 1.10 | 30 | 4.0 | 0 |
| Comparative Example 6 | 1.0 | not used | | $n-C_6H_{14}$ | 150 | 1.05 | 10 | 3.0 | 0 |

COMPARATIVE EXAMPLES 7 TO 9

Other experiments were carried out under the same condition as in Example 1, except that 1,3-diethinyl-1,1,3,3-tetramethyldisiloxane was replaced with bis(-

* * * * *